(12) United States Patent
Albrecht et al.

(10) Patent No.: US 9,593,068 B2
(45) Date of Patent: Mar. 14, 2017

(54) DERIVATIVES OF TARTARIC ACID

(71) Applicant: RATIOPHARM GMBH, Ulm (DE)

(72) Inventors: Wolfgang Albrecht, Ulm (DE); Roland Selig, Ulm (DE); Sebastian Rabe, Neu-Ulm (DE); Annemarie Maier, Biberach (DE); Richard Guserle, Kötz (DE)

(73) Assignee: ratiopharm GmbH, Ulm (DE)

( * ) Notice: Subject to any disclaimer, the term of this patent is extended or adjusted under 35 U.S.C. 154(b) by 0 days.

(21) Appl. No.: 15/037,667

(22) PCT Filed: Dec. 4, 2014

(86) PCT No.: PCT/EP2014/076517
§ 371 (c)(1),
(2) Date: May 18, 2016

(87) PCT Pub. No.: WO2015/082588
PCT Pub. Date: Jun. 11, 2015

(65) Prior Publication Data
US 2016/0326090 A1 Nov. 10, 2016

(30) Foreign Application Priority Data

Dec. 5, 2013 (EP) .................................... 13005679
May 28, 2014 (EP) .................................... 14170158
Dec. 20, 2014 (EP) .................................... 13198725

(51) Int. Cl.
*A61K 31/40* (2006.01)
*C07D 207/40* (2006.01)
*C07C 69/708* (2006.01)
*C07C 69/60* (2006.01)
*C07C 69/67* (2006.01)
*C07C 219/08* (2006.01)

(52) U.S. Cl.
CPC ............ *C07C 69/708* (2013.01); *C07C 69/60* (2013.01); *C07C 69/67* (2013.01); *C07C 219/08* (2013.01)

(58) Field of Classification Search
CPC .............................. A61K 31/40; C07D 207/40
See application file for complete search history.

(56) References Cited

U.S. PATENT DOCUMENTS 8,148,414 B2 * 4/2012 Gangakhedkar ........ C07C 69/60
514/237.5

OTHER PUBLICATIONS

PCT/EP2014/076517, Int'l Preliminary Report on Patentability & Written Opinion of the ISA, Jun. 7, 2016.
PCT/EP2014/076517, Int'l Search Report, Feb. 26, 2015.

* cited by examiner

*Primary Examiner* — Shirley V Gembeh
(74) *Attorney, Agent, or Firm* — Milstein Zhang & Wu LLC

(57) ABSTRACT

The present invention relates to novel compounds, e.g. for use as a medicament. In particular, the present invention relates to novel medicaments, preferably in the treatment and/or prevention of systemic diseases, autoimmune diseases, and/or inflammatory diseases, for example multiple sclerosis and psoriasis.

18 Claims, 2 Drawing Sheets

DERIVATIVES OF TARTARIC ACID

The present invention relates to novel compounds, e.g. for use as a medicament. In particular, the present invention relates to novel prodrugs of monomethyl fumarate (MMF) suitable as a medicament, preferably in the treatment and/or prevention of systemic diseases, autoimmune diseases, and/or inflammatory diseases, for example multiple sclerosis and psoriasis. Further, the invention relates to a pharmaceutical composition comprising said compounds.

BACKGROUND OF THE INVENTION

Dimethyl fumarate (DMF) is an oral therapeutic agent which is reported to reduce the rejection often occurring in connection with organ transplantation (host versus graft reaction). Further, DMF is approved to be suitable as medicament for the treatment or prevention of a variety of diseases. For example, DMF is proposed in the treatment of autoimmune diseases such as multiple sclerosis. Further, DMF is suggested to be a suitable active pharmaceutical agent in the treatment of psoriasis. DMF is characterized by the following chemical Formula (1):

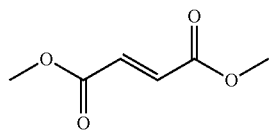

Formula (1)

When taken orally DMF is reported to be hydrolyzed for example by the acidic ambience of the stomach or by esterases in the intestine to monomethyl fumarate (MMF). MMF can be regarded as a metabolite of DMF and can be characterized by the following chemical Formula (2):

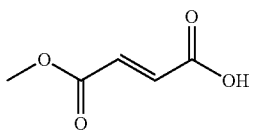

Formula (2)

The mechanisms of action of DMF or its metabolite MMF is reported to include inhibition of cytokine-induced nuclear translocation of the nuclear factor kappa B (NF-κB)), apoptosis of stimulated T cells, and increased production of the $T_h2$ cytokines IL-4 and IL-5 in stimulated T cells, whereas generation of the $T_h1$ cytokine interferon gamma (IFN-γ) is supposed to remain unaffected. DMF is described to activate the transcription factor Nrf2 (nuclear factor erythroid 2-related factor 2), which binds to antioxidant response elements in the promoters of protective genes such as NADPH-quinone-oxidoreductase-1 (NQO1) and heme-oxygenase-1. Thus, this ultimately raises the levels of the important intracellular antioxidant glutathione (cf. Albrecht P. et al., Journal of Neuroinflammation 2012, 9:163).

Further, it is alleged that the treatment of animals or primary cultures of CNS cells with DMF or MMF resulted in increased nuclear levels of active Nrf2, with subsequent up-regulation of canonical antioxidant target genes. DMF or MMF treatment increased cellular redox potential, glutathione, ATP levels, and mitochondrial membrane potential in a concentration-dependent manner. Treating astrocytes or neurons with DMF or MMF also significantly improved cell viability after toxic oxidative challenge in a concentration-dependent manner. This effect on viability was lost in cells that had eliminated or reduced Nrf2. These data suggest that DMF and MMF are cytoprotective for neurons and astrocytes against oxidative stress-induced cellular injury and loss, potentially via up-regulation of an Nrf2-dependent antioxidant response. Thus, in summary, it is indicated that in vivo DMF and MMF show about the same the efficacy, in particular on the transcription factor Nrf2.

As mentioned above, when taken orally DMF is rather rapidly hydrolyzed for example by the acidic ambience of the stomach or by esterases in the intestine to monomethyl fumarate (MMF). Thus, significant amounts of MMF are released within a short period of time. Such a rapid hydrolysis in principle was expected to provide a high level of MMF in the plasma within a short period of time.

However, it has been found that a high MMF plasma level might not be achievable. For example the organism might not be capable of transferring the small amount of MMF to the sites of the body where the pharmacological action takes place.

Additionally, it is reported that DMF has to be administered in quite high amounts and that the pharmaceutically active agent often shows undesirable side effects such as flush and especially symptoms related to the gastrointestinal tract such as irritation of the stomach and diarrhoea.

Consequently, there is still a need for new compounds, preferably for use as a medicament, more preferably in the treatment and/or prevention of systemic diseases, autoimmune diseases, and/or inflammatory diseases, for example multiple sclerosis and psoriasis. The medicaments should be capable of being applied in appropriate doses and should not cause significant undesired side effects.

Hence, it was an object of the present invention to overcome the drawbacks of the above-mentioned market drug substance DMF.

It was an object to develop a compound to be used as a medicament for the above-mentioned diseases wherein said compound shows advantageous pharmacokinetic properties.

Moreover, compounds should be provided which are hydrolysed to MMF more slowly than DMF in the human body (or under respective in-vitro conditions).

Further, the compounds should preferably cause few undesirable side effects.

Additionally, it was an object of the present invention to provide compounds which can be used in the treatment of the early phase of an autoimmune disease, in particular of multiple sclerosis, such that the progress of the disease can be delayed.

SUMMARY OF THE INVENTION

Figure 1:
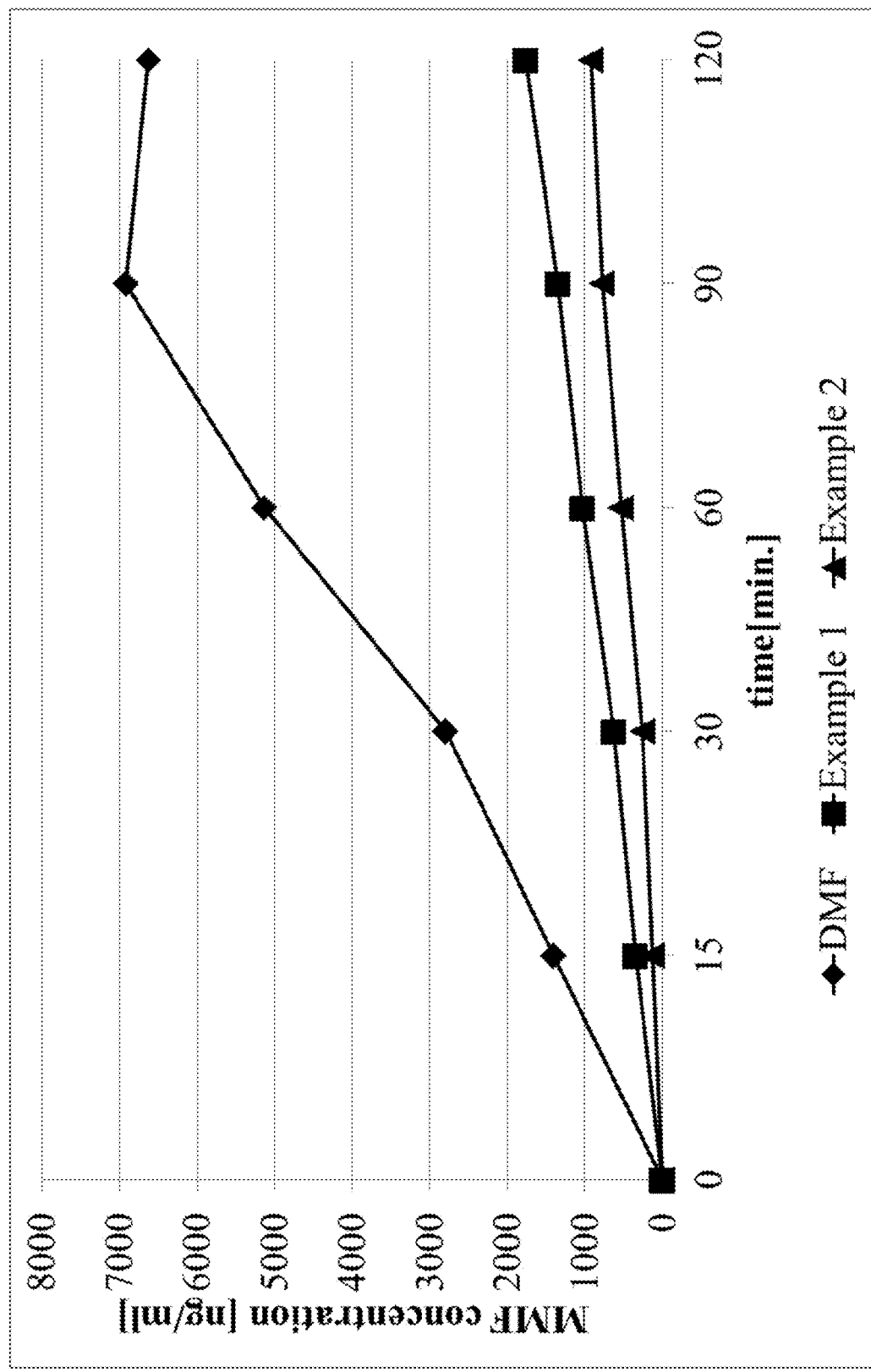
FIG. 1 shows a modified hydrolyzation for the compounds of Examples 1 and 2 as compared to DMF.

According to the present invention, the above objectives are achieved by the specific compounds described herein by Formulae (I) or (II). Said compounds can be used as a medicament for the treatment and/or prevention of systemic diseases, autoimmune diseases, and/or inflammatory diseases, for example multiple sclerosis and psoriasis.

The compounds of the invention can be regarded as MMF prodrugs. Generally, a prodrug can be regarded as a substance that is administered to a subject (preferably human) in a pharmacologically inactive or pharmacologically less than fully active form, and is subsequently converted in the body of the subject to an active drug, preferably through metabolic processes occurring in the body of the subject. In other words, a prodrug usually serves as a type of 'precursor' to the intended drug.

Thus, the subject of the present invention is a compound according to the following Formula (I) or (II):

Formula (I)

wherein
$R^1$ is $OR^{1'}$ or $NR^{1''}R^{1'''}$, wherein $R^{1'}$ is hydrogen, alkyl with 1 to 6 carbon atoms, or cyclic alkyl with 3 to 6 carbon atoms, or wherein $R^{1''}$ and $R^{1'''}$ independently are hydrogen, alkyl with 1 to 6 carbon atoms, or cyclic alkyl with 3 to 6 carbon atoms,
and
$R^2$ is $OR^{2'}$ or $NR^{2''}R^{2'''}$, wherein $R^{2'}$ is hydrogen, alkyl with 1 to 6 carbon atoms, or cyclic alkyl with 3 to 6 carbon atoms, or wherein $R^{2''}$ and $R^{2'''}$ independently are hydrogen, alkyl with 1 to 6 carbon atoms, or cyclic alkyl with 3 to 6 carbon atoms,
or
$R^1$ and $R^2$ together are $NR^{12}$ forming a cyclic imide, wherein $R^{12}$ is hydrogen, alkyl with 1 to 6 carbon atoms, or cyclic alkyl with 3 to 6 carbon atoms,
or Formula (II)

wherein
$R^3$ and $R^4$ are each independently —$(CH_2)_{n'}$—$OR^5$ or —$(CH_2)_{n''}$—CO—$R^6$, wherein
n' and n" are each independently 1, 2, or 3,
$R^5$ is hydrogen or trans —CO—CH=CH—COOCH$_3$,
$R^6$ is $OR^7$ wherein $R^7$ is hydrogen or alkyl with 1 to 4 carbon atoms, or $NR^8R^9$, wherein $R^8$ and $R^9$ are each independently hydrogen or alkyl with 1 to 4 carbon atoms, optionally with the proviso that $R^3$ and $R^4$ are not both trans —$(CH_2)_2$—O—CO—CH=CH—COOCH$_3$.

Generally, the compounds according to formula (I) or (II) encompass pharmaceutically acceptable salts, hydrates, solvates and/or polymorphs of said compounds.

It was found that the compounds of the present invention show superior pharmaceutical and/or pharmacokinetic properties. In particular, the compounds show an advantageous rate of hydrolysis rate so that the appropriate dose of the compound can be applied to the patient.

Another subject of the invention is a compound according to Formula (I) or (II) for use as a medicament.

Further, the present invention relates to a compound according to Formula (I) or (II) for use in the treatment of systemic diseases, autoimmune diseases and/or inflammatory diseases, preferably for use in the treatment of multiple sclerosis or psoriasis, in particular multiple sclerosis.

Another subject is a pharmaceutical composition comprising the above-mentioned compound according to Formula (I) or (II).

Another subject of the present invention is the process for producing a compound according to Formula (I) by reacting monomethyl fumarate with the two hydroxy groups of 2,3-dihydroxybutanedioic acid derivative.

DETAILED DESCRIPTION OF THE INVENTION

In the context of this invention, the compound of the present invention is represented by the above Formula (I) or (II). Further, the compound may refer to pharmaceutically acceptable salts, hydrates, solvates, polymorphs, stereoisomers and mixtures thereof. For example, the invention also refers to pharmaceutically acceptable salts of compounds according to Formula (I) or (II) or to solvates of salts or hydrates of polymorphs or the like. The same applies to all embodiments, e.g. to compounds as shown below.

It is preferred that the compound according to Formula (I) is present in the L-(+)-form or as racemate, in particular in the L-(+)-form.

In a particularly preferred embodiment of the present invention a single compound according to Formula (I) or (II) can be used as a medicament.

The same applies to the pharmaceutical composition comprising the compound(s) represented by Formula (I) or (II).

A first aspect of the invention relates to compounds according to Formula (I). In a preferred embodiment of the said first aspect in Formula (I)
$R^1$ is $OR^{1'}$ or $NR^{1''}R^{1'''}$, wherein $R^{1'}$ is hydrogen, alkyl with 1 to 6 carbon atoms or cyclic alkyl with 3 to 6 carbon atoms, or wherein $R^{1''}$ and $R^{1'''}$ independently are hydrogen, alkyl with 1 to 6 carbon atoms or cyclic alkyl with 3 to 6 carbon atoms,
and
$R^2$ is $OR^{2'}$ or $NR^{2''}R^{2'''}$, wherein $R^{2'}$ is hydrogen, alkyl with 1 to 6 carbon atoms or cyclic alkyl with 3 to 6 carbon atoms, or wherein $R^{2''}$ and $R^{2'''}$ independently are hydrogen, alkyl with 1 to 6 carbon atoms or cyclic alkyl with 3 to 6 carbon atoms
or
$R^1$ and $R^2$ together are $NR^{12}$ forming a cyclic imide, wherein $R^{12}$ is hydrogen, alkyl with 1 to 6 carbon atoms or cyclic alkyl with 3 to 6 carbon atoms.

Alkyl with 1 to 6 carbon atoms can for example include methyl, ethyl, propyl, isopropyl, butyl, isobutyl, tert.butyl, pentyl, sec.-pentyl, and hexyl.

Cyclic alkyl with 3 to 6 carbon atoms can for example include cyclopropyl, cyclobutyl, cyclopentyl and cyclohexyl.

In a preferred embodiment $R^1$ is $OR^{1'}$ and $R^2$ is $OR^{2'}$, wherein $R^{1'}$ and $R^{2'}$ are independently hydrogen, alkyl with 1 to 6 carbon atoms or cyclic alkyl with 3 to 6 carbon atoms, preferably alkyl with 1 to 3 carbon atoms, cyclic alkyl with 3, 5 or 6 carbon atoms, more preferably alkyl with 1 to 3 carbon atoms.

Preferably $R^1$ is $OR^{1'}$ and $R^2$ is $OR^{2'}$ wherein $OR^{1'}$ and $OR^{2'}$ are identical. It is further preferred that $R^{1'}$ and $R^{2'}$ are hydrogen, alkyl with 1 to 6 carbon atoms or cyclic alkyl with 3 to 6 carbon atoms, preferably hydrogen, alkyl with 1 to 3 carbon atoms cyclic alkyl with 3, 5 or 6 carbon atoms. In a more preferred embodiment $R^{1'}$ and $R^{2'}$ are hydrogen or alkyl with 1 to 3 carbon atoms.

In a further preferred embodiment the compound of the invention is selected from the compounds according to any one of Formulae (Ia) to (Ic)

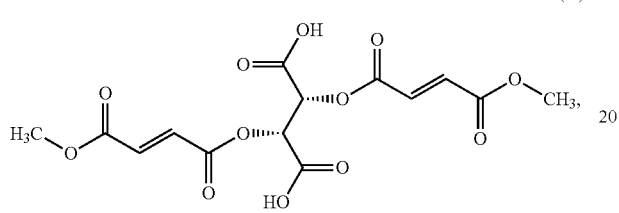

Formula (Ia)

Formula (Ib)

Formula (Ic)

In an alternative preferred embodiment $R^1$ is $NR^{1''}R^{1'''}$ and $R^2$ is $NR^{2''}R^{2'''}$, wherein $R^{1''}$ and $R^{1'''}$ independently can be hydrogen, alkyl with 1 to 6 carbon atoms or cyclic alkyl with 3 to 6 carbon atoms, and wherein $R^{2''}$ and $R^{2'''}$ independently can be hydrogen, alkyl with 1 to 6 carbon atoms or cyclic alkyl with 3 to 6 carbon atoms. It is more preferred that $R^{1''}$, $R^{1'''}$, $R^{2''}$ and $R^{2'''}$ independently can be hydrogen, alkyl with 1 to 3 carbon atoms or cyclic alkyl with 3, 5 or 6 carbon atoms, more preferably hydrogen or alkyl with 1 to 3 carbon atoms.

It is further preferred that one of $R^{1''}$ and $R^{1'''}$ and one of $R^{2''}$ and $R^{2'''}$ are hydrogen. It is further preferred that the other two residues are alkyl, preferably alkyl with 1 to 3 carbon atoms.

It is alternatively preferred that $R^{1''}$, $R^{1'''}$, $R^{2''}$ and $R^{2'''}$ are identical and it is further preferred that they are hydrogen or alkyl with 1 to 3 carbons atoms.

Alternatively, $R^1$ and $R^2$ together are $NR^{12}$ forming a cyclic imide, wherein $R^{12}$ can be hydrogen, alkyl with 1 to 6 carbon atoms or cyclic alkyl with 3 to 6 carbon atoms, preferably hydrogen or alkyl with 1 to 4 carbon atoms. In case that $R^1$ and $R^2$ together are $NR^{12}$, the cyclic imide which is formed can be represented by the following Formula (Id)

Formula (Id)

The compound according to Formula (I) further encompasses all stereoisomers of the compound according to Formula (I) as well as the racemate.

The compound according Formula (I) can be represented by two monomethyl fumarate residues which are coupled to the two hydroxyl groups of 2,3-hydroxy butanedioic acid diester, 2,3-hydroxy butanedioic acid monoester monoamide, 2,3-hydroxy butanedioic acid diamide or 2,3-hydroxy butandioic acid imide.

A compound according to Formula (I) can preferably be synthesized via the following route:

Formula (I)

Preferably, in step a, MMF and the 2,3-dihyhydroxy butanedioic acid derivative can be submitted to an esterification in an organic solvent in the presence of a coupling agent. A coupling agent is preferably a substance generally facilitating the formation of an ester or an amide. The coupling agent reacts with a carboxy group by forming a reactive intermediate which is subsequently further reacted with an alcohol or an amine to form the final product, i.e. an ester or an amide. Coupling agents are reported to be used in case that one or both of the educts further bear a group being labile in acidic or alkaline milieu, since the reaction is carried out under neutral conditions. Suitable coupling agents can be for example DCC (N,N'-dicyclohexylcarbodiimide), DIC (N,N'-diisopropylcarbodiimide), EDC (N-ethyl-N'-(3-methylaminopropyl)carbodiimide hydrochloride), CDI (carbonyldiimidazole), preferably EDC. It is further preferred that the coupling reaction is carried out in the presence of an auxiliary alkaline compound. Suitable alkaline compounds are for example pyridine and amines, such as triethylamine, and diisopropylethylamine and DMAP (4-(dimethylamino)pyridine), in particular DMAP.

A suitable organic solvent can for example be dichloromethane, chloroform, acetonitrile, dioxane, tetrahydrofuran and dimethylformamide.

Alternatively, MMF can be preferably reacted with thionyl chloride or oxalyl chloride, preferably oxalyl chloride, to form the corresponding acid chloride. Subsequently, the corresponding acid chloride can be submitted to a reaction with a 2,3-dihyhydroxy butanedioic acid derivative, preferably in an organic solvent such as dioxane, tetrahydrofuran, chloroform or dichloromethane. Further, the reaction of the acid chloride with the 2,3-dihyhydroxy butanedioic acid derivative is preferably carried in the presence of an auxiliary alkaline compound. Suitable alkaline compounds are for example pyridine and amines, such as triethylamine, and diisopropylethylamine, preferably triethylamine.

Alternatively, the above acid chloride of MMF can be further transferred in activated esters like the para-nitrophenol ester.

Further alternatively, MMF can be reacted with acid chlorides, diphenylphosphoryl azide or chlorosulfonyl isocyanate to form (mixed) anhydrides. These mixed anhydrides can be also submitted to further reactions to obtain further forms of anhydrides. For example, the dimeric anhydride of dimethylfumarate can be obtained by said preparation.

Subsequently, an activated ester of MMF anhydride can be submitted to a reaction with the 2,3-dihyhydroxy butanedioic acid derivative, preferably in an organic solvent such as dioxane, tetrahydrofuran, chloroform, acetone or dichloromethane. Further, the reaction of an activated ester of MMF anhydride with the 2,3-dihyhydroxy butanedioic acid derivative is preferably carried out in the presence of an auxiliary alkaline compound. Suitable alkaline compounds are for example pyridine and amines, such as triethylamine, diisopropylethylamine and DMAP (4-(dimethylamino)pyridine), preferably DMAP.

The above compounds according to Formula I show excellent pharmacokinetic properties. Within two hours the compounds show a hydrolysis into MMF and remaining organic residue wherein the hydrolysis is significantly slower than the one of DMF. As a result, a smaller amount of MMF is released within the two hours and thus the compounds can be referred to as compounds (prodrugs of MMF) with an intrinsically retarded release of MMF. Additionally, the remaining organic residue is not expected to harm the patient's organism.

In second aspect, the present invention relates to a compound according to Formula (II). In a preferred embodiment of said aspect, in Formula (II)

$R^3$ and $R^4$ are each independently —$(CH_2)_{n'}$—$OR^5$ or —$(CH_2)_{n''}$—CO—$R^6$, wherein n' and n" are each independently 1, 2 or 3, $R^5$ is hydrogen or trans —CO—CH═CH—$COOCH_3$, $R^6$ is hydrogen, alkyl with 1 to 4 carbon atoms, —$OR^7$ wherein $R^7$ is hydrogen or alkyl with 1 to 4 carbon atoms, or —$NR^8R^9$, wherein $R^8$ and $R^9$ are each independently hydrogen or alkyl with 1 to 4 carbon atoms.

Alkyl with 1 to 4 carbon atoms can for example include methyl, ethyl, propyl, isopropyl, butyl, isobutyl, and tert-.butyl.

In a preferred embodiment $R^3$ and $R^4$ are —$(CH_2)_{n'}$—$OR^5$ wherein n' is independently 1, 2 or 3, and $R^5$ is hydrogen or trans —CO—CH═CH—$COOCH_3$. In case that $R^3$ and $R^4$ are both —$(CH_2)_{n'}$—$OR^5$, it is not mandatory that $R^3$ and $R^4$ are the same residue. For example $R^3$ can be —$(CH_2)_{n'}$—$OR^5$ with n' being 2 and $R^5$ being hydrogen while $R^4$ can be —$(CH_2)_{n'}$—$OR^6$ with n' being 1 and $R^5$ being trans —CO—CH═CH—$COOCH_3$.

Preferably, n' can be 2 or 3, in particular n' is 2.

In a further preferred embodiment at least one of $R^3$ and $R^4$ is —$(CH_2)_2$—OH. It turned out that an advantageous water solubility of the inventive compound can be obtained if at least one residue of $R^3$ and $R^4$ is a —$(CH_2)_2$—OH group.

Preferably, $R^3$ and $R^4$ both can be —$(CH_2)_2$—OH.

Alternatively, it is preferred that one of $R^3$ and $R^4$ is —$(CH_2)_2$—OH and the other one of $R^3$ and $R^4$ is trans —$(CH_2)_2$—O—CO—CH═CH—$COOCH_3$.

It is particularly preferred that a compound according to the present invention can be selected from a compound according Formula (IIa) or (IIb)

Formula (IIa)
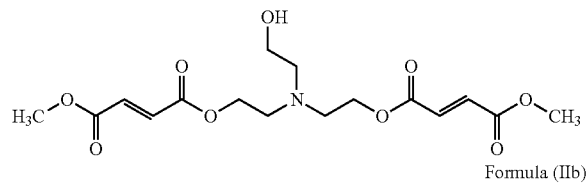

Formula (IIb)
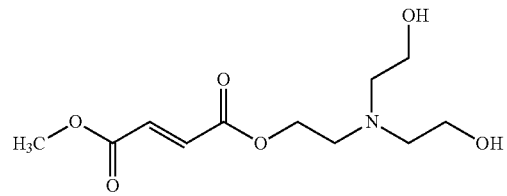

In an alternative preferred embodiment at least one of $R^3$ and $R^4$ can be —$(CH_2)_{n''}$—CO—$R^6$, wherein n" is independently 1, 2 or 3, and $R^6$ is hydrogen, alkyl with 1 to 4 carbon atoms, $OR^7$ wherein $R^7$ is hydrogen or alkyl with 1 to 4 carbon atoms, or $NR^8R^9$, wherein $R^8$ and $R^9$ are each independently hydrogen or alkyl with 1 to 4 carbon atoms. Preferably $R^6$ is $OR^7$ wherein $R^7$ is hydrogen or alkyl with 1 to 4 carbon atoms, or $NR^8R^9$, wherein $R^8$ and $R^9$ are each independently hydrogen or alkyl with 1 to 4 carbon atoms.

In case that $R^3$ and $R^4$ are both —$(CH_2)_{n''}$—CO—$R^6$, it is not mandatory that $R^3$ and $R^4$ are the same residue. For example $R^3$ can be —$(CH_2)_{n''}$—CO—$R^6$ with n" being 2 and $R^6$ being hydrogen while $R^4$ can be —$(CH_2)_{n''}$—CO—$R^6$ with n" being 1 and $R^6$ being $OR^7$ wherein $R^7$ is alkyl with 1 to 4 carbon atoms.

In a preferred embodiment n" can be 1 or 2, in particular 1.

Preferably, $R^6$ can be $OR^7$ with $R^7$ being hydrogen or alkyl with 1 to 4 carbon atoms. It is preferred that $R^7$ is hydrogen or alkyl with 1 or 2 carbon atoms.

Thus, an inventive compound with n" being 1 and $R^6$ being $OR^7$ with $R^7$ being hydrogen or alkyl with 1 or 2 carbon atoms can be regarded as a substituted acetic acid derivative or as a substituted acetic acid ester derivative, respectively.

Alternatively preferably, $R^6$ can be $NR^8R^9$, wherein $R^8$ and $R^9$ are each independently hydrogen or alkyl with 1 to 4 carbon atoms. It is preferred that $R^8$ and $R^9$ are independently hydrogen or alkyl with 1 or 2 carbon atoms. Preferably at least one of $R^8$ and $R^9$ is hydrogen.

Thus, an inventive compound with n" being 1 and $R^6$ being $NR^8R^9$ with $R^8$ and $R^9$ being hydrogen or alkyl with 1 or 2 carbon atoms can be regarded as a substituted acetic acid amide derivative.

A compound according to Formula (I) can preferably be synthesized via the following route:

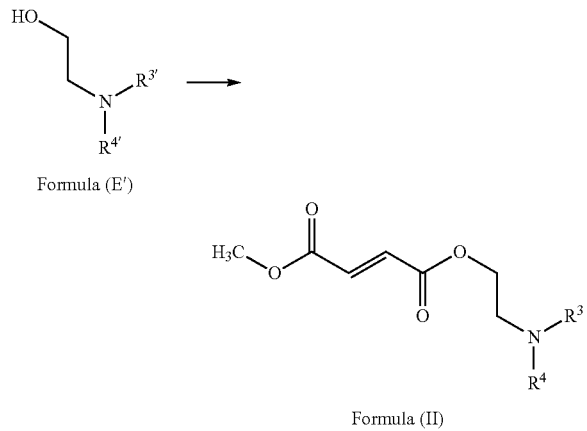

In a compound according to Formula (E') $R^{3'}$ and $R^{4'}$ generally correspond to $R^3$ and $R^4$ as defined above, respectively. However, in case that $R^{3'}$ and/or $R^{4'}$ are $-(CH_2)_{n'}-$OH they might or might not be submitted to an esterification with MMF corresponding to the one as described below to obtain the respective $R^3$ and $R^4$ residue.

Preferably, in the above reaction a compound according to Formula (E') and MMF can be submitted to an esterification in an organic solvent in the presence of a coupling agent. A coupling agent is preferably a substance generally facilitating the formation of an ester or an amide. The coupling agent reacts with a carboxy group by forming a reactive intermediate which is subsequently further reacted with an alcohol or an amine to form the final product, i.e. an ester or an amide. Coupling agents are reported to be used in case that one or both of the educts further bear a group being labile in acidic or alkaline milieu, since the reaction is carried out under neutral conditions. Suitable coupling agents can be for example DCC (N,N'-dicyclohexylcarbodiimide), DIC (N,N'-diisopropylcarbodiimide), EDC (N-ethyl-N'-(3-methylaminopropyl)carbodiimide hydrochloride), CDI (carbonyldiimidazole), preferably EDC. It is further preferred that the coupling reaction is carried out in the presence of an auxiliary alkaline compound. Suitable alkaline compounds are for example pyridine and amines, such as triethylamine, and diisopropylethylamine and DMAP (4-(dimethylamino) pyridine), in particular DMAP.

A suitable organic solvent can for example be dichloromethane, chloroform, acetonitrile, dioxane, tetrahydrofuran and dimethylformamide.

Alternatively, MMF can be preferably reacted with thionyl chloride or oxalyl chloride, preferably oxalyl chloride, to form the corresponding acid chloride. Subsequently, the corresponding acid chloride can be submitted to a reaction with the compound according to Formula (E'), preferably in an organic solvent such as dioxane, tetrahydrofuran, chloroform or dichloromethane. Further, the reaction of the acid chloride with a compound according to Formula (E') is preferably carried out in the presence of an auxiliary alkaline compound. Suitable alkaline compounds are for example pyridine and amines, such as triethylamine, and diisopropylethylamine, preferably triethylamine.

Alternatively, the above acid chloride of MMF can be further transferred in activated esters like the para-nitrophenol ester.

Further alternatively, MMF can be reacted with acid chlorides, diphenylphosphoryl azide or chlorosulfonyl isocyanate to form (mixed) anhydrides. These mixed anhydrides can be also submitted to further reactions to obtain further forms of anhydrides. For example, the dimeric anhydride of dimethylfumarate can be obtained by said preparation.

Subsequently, an activated ester of MMF anhydride can be submitted to a reaction with the compound according to Formula (E'), preferably in an organic solvent such as dioxane, tetrahydrofuran, chloroform, acetone or dichloromethane. Further, the reaction of an activated ester of MMF anhydride with the compound according to Formula (E') is preferably carried out in the presence of an auxiliary alkaline compound. Suitable alkaline compounds are for example pyridine and amines, such as triethylamine, diisopropylethylamine and DMAP (4-(dimethyl-amino)pyridine), preferably DMAP.

Alternatively, the reaction of the activated ester of MMF anhydride with the compound according to Formula (E') can preferably be carried out in the absence of an auxiliary alkaline compound.

A suitable organic solvent can for example be dioxane, tetrahydrofuran and dimethylformamide.

In a preferred embodiment one of the hydroxy groups of the compound according to Formula (E') can be protected with a protection group before being submitted to a reaction with MMF in the presence of a coupling agent or with the acid chloride of MMF. Such a protection group can for example be a trialkylsilyl group.

After the coupling reaction the protection can preferably be removed by a suitable reaction.

The compounds according to Formula (II) show superior pharmaceutical and/or pharmacokinetic properties. In particular, the compounds show an advantageous hydrolyzation rate so that the appropriate dose of the compound can be applied to the patient.

Further, the present invention relates to the inventive compounds according to Formula (I) or (II) for use as a medicament.

A further subject of the invention is the inventive compounds according to Formula (I) or (II) for use in the treatment and/or prevention of systemic diseases, autoimmune diseases or inflammatory diseases.

Systemic diseases do not just affect single organs. Instead, these diseases are known to affect a number of organs and tissues or even the body as a whole.

People having an autoimmune disease usually suffer from their immune system mistakenly attacking their own cells of their organism and thus incorrectly responding to substances normally present in the body.

An inflammation can be defined as the response of the body to the occurrence of harmful stimuli which can result in pain, heat, redness, swelling and loss of function of the affected organ.

It is possible that some of the above-mentioned diseases cannot be allocated in one single group of the above-mentioned groups, since they show the symptoms of more than one of them.

In a further preferred embodiment, the inventive compound according to Formula (I) or (II) is for use in the treatment of multiple sclerosis and psoriasis, preferably multiple sclerosis. The compounds of the present invention can e.g. be used in the treatment of the following types of multiple sclerosis: relapsing-remitting, primary-progressive, secondary-progressive, and progressive-relapsing. In a preferred embodiment the compounds of the present invention are used in the treatment of relapsing-remitting multiple sclerosis.

Further, the present invention also provides a pharmaceutical composition comprising the compound according to the present invention, i.e. a pharmaceutical composition comprising a compound according to Formula (I) or (II) and optionally pharmaceutical excipients.

In a preferred embodiment the pharmaceutical composition comprises
(i) 0.01 to 10 mmol, more preferably 0.05 to 5 mmol, still more preferably 0.25 to 3.5 mmol and particularly preferred 0.5 to 2.5 mmol of a compound according to Formula (I) or (II);
(ii) pharmaceutical excipient(s).

In a further preferred embodiment the present composition can comprise one or more further excipients, preferably pharmaceutical excipients as described in the European Pharmacopoeia (Ph.Eur.) and/or in the US Pharmacopoeia (USP).

Examples of pharmaceutical excipients are carriers, binders, fillers, disintegrants, wicking agents, glidants and/or lubricants.

In a preferred embodiment the excipients are chosen such that the resulting formulation is a gastric juice-resistant formulation. In a preferred embodiment the formulation of the present invention does not show significant drug release under acidic conditions. In particular, the in-vitro drug release after 2 hours is less than 10%, preferably 0 to 9.9%, more preferably 0 to 5%, still more preferably 0.001 to 3%, measured according to USP, Apparatus II, paddle, 0.1 N HCl, 37° C., 50 rpm. The pharmaceutical composition can be in a form suitable for oral administration, preferably in the form of a tablet or capsule, in particular in form of a tablet.

It is further preferred that the tablet is coated with a film coating. Alternatively, the capsule could also be coated.

In the present invention, the following three types of film coatings are possible:
film coating without affecting the release of the active ingredient,
gastric juice-resistant film coatings,
retard film coatings.

Generally, film coatings can be prepared by using film-forming agents such as waxes, cellulose derivatives, poly (meth)acrylate, polyvinylpyrrolidone, polyvinyl acetate phthalate, and/or shellac or natural rubbers such as carrageenan.

It is preferred that the present tablet is coated with a gastric juice-resistant film coating. Alternatively, a capsule comprising a gastric juice-resistant film coating can be used.

The gastric juice-resistant film coating preferably is a film coating being stable in the pH range of about 0.7 to 3.0, which is supposed to be the pH-value of human gastric juice found in the stomach. However, in an environment with a pH value of 5 to 9, which is supposed to be present in the (small) intestine of the human body, the gastric juice-resistant film coating preferably dissolves and the drug can be released.

The gastric juice-resistant film coating (often also referred to as enteric coating) can comprise film-forming agents being for example fats, fatty acids, waxes, alginates, shellac, polyvinyl acetate phthalate, cellulose derivatives such as carboxy methyl ethyl cellulose, cellulose acetate succinate, cellulose acetate phthalate, hydroxypropyl methyl cellulose phthalate, hydroxypropyl methyl cellulose acetate succinate, cellulose acetate trimellitate, and meth(acrylic)acid copolymers such as methyl acrylate-methacrylic acid copolymers, methyl methacrylate-methacrylic acid copolymers, Eudragits (for example Eudragit® L30D, Eudragit® L, Eudragit® S).

The coating is preferably free of active ingredient. It is further preferred that the thickness of the coating is usually 10 μm to 2 mm, preferably from 50 to 500 μm.

The preferred coating may comprise a film-forming agent and one or more of the following: lubricant, surfactant, glidant, pigment and water.

The preferred coating according to an embodiment of the present invention can comprise, along with the film-forming agent, e.g. stearic acid as lubricant for plasticizing and dissolving the polymer, sodium lauryl sulfate as a surfactant for wetting and dispersing, talc as glidant, iron oxide yellow and/or titanium oxide as pigment(s) and optionally purified water.

In a preferred embodiment the pharmaceutical composition can be administered one to three times a day, preferably once or twice a day, more preferably once a day.

Further, the present invention relates to a method for treating and/or preventing systemic diseases, autoimmune diseases and/or inflammatory diseases, preferably multiple sclerosis or psoriasis, in particular multiple sclerosis, comprising administering to a subject in need thereof a therapeutically effective amount of the compound of the invention or the pharmaceutical composition of the invention. For the compound and the pharmaceutical composition administered in the before-mentioned method the same applies as to the compound and the pharmaceutical composition as described above in the text, respectively.

The invention is illustrated by the following examples.

EXAMPLES

Example 1

Synthesis of (E)-But-2-enedioic acid (1R,2R)-1,2-bis-ethoxy-carbonyl-2-((E)-3-methoxy carbonyl-acryloyloxy)-ethyl ester methyl ester

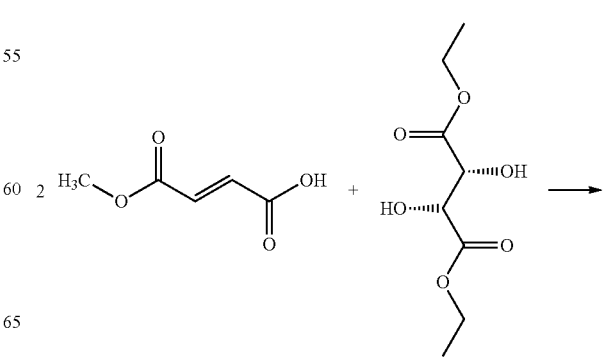

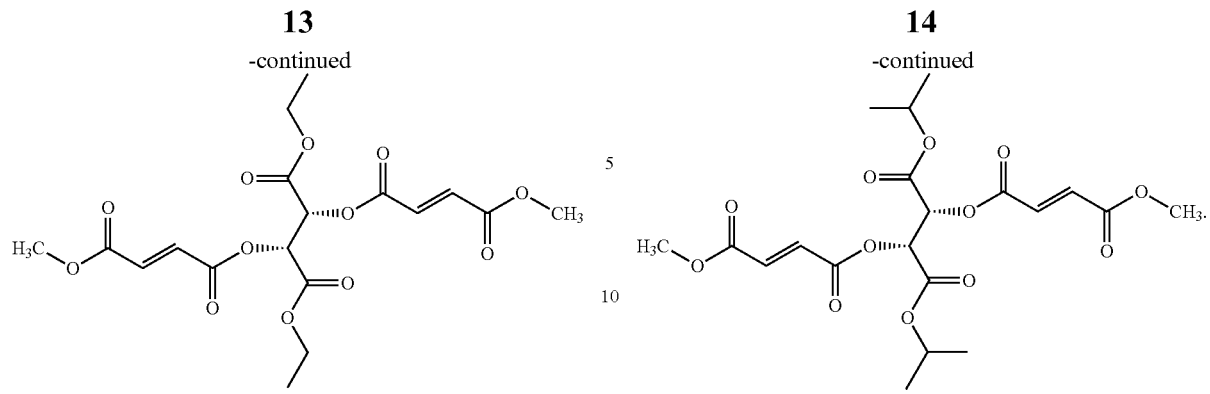

Monomethyl fumarate (1.5 g; 11.5 mmol), diethyl tartrate (0.71 g, 3.5 mmol), N-ethyl-N'-(3-methylaminopropyl)carbodiimide hydrochloride (EDC) (2.21 g, 11.5 mmol) and 4-(dimethylamino)pyridine (DMAP) (70 mg, 0.6 mmol) were dissolved in dry dichloromethane (30 ml). The reaction mixture was kept under continuous stirring at room temperature for 22.5 h. The organic layer was washed 2 times with water (2×50 ml), the aqueous layer was washed with dichloromethane (50 ml) and the combined organic layers were dried over anhydrous sodium sulfate, filtered, and concentrated in vacuo at 41° C. The black oily product was subjected to column chromatography (eluent: EtOAc/n-hexane 1/1). A colorless oil resulted which solidified to a white solid.

Yield: 305 mg (0.7 mmol); 20% of theory $^{1}$H NMR (400 MHz, CDCl$_{3}$) δ ppm 1.24 (t, J=7.04 Hz, 6 H) 3.83 (s, 6 H) 4.24 (t, J=6.84 Hz, 4 H) 5.84 (s, 2 H) 6.95 (s, 3 H)

IR (ATR) [cm$^{-1}$] 3091, 2997, 2951, 2912, 2850, 1765, 1741, 1716, 1659, 1479, 1439, 1373, 1350, 1321, 1292, 1265, 1240, 1209, 1132, 1059, 1032, 1022, 1009, 976, 924, 872, 771, 712, 671

Example 2

((E)-But-2-enedioic acid (1R,2R)-1,2-bis-isopropoxycarbonyl-2-((E)-3-methoxycarbonyl-acryloyloxy)-ethyl ester methyl ester)

Monomethyl fumarate (3 g; 23.06 mmol), diisopropyl tartrate (1.62 g, 6.9 mmol), N-ethyl-N'-(3-methylaminopropyl)carbodiimide hydrochloride (EDC) (4.42g, 23.1 mmol) and 4-(dimethylamino)pyridine (DMAP) (140 mg, 1.2 mmol) were dissolved in dry dichloromethane (60 ml). The reaction mixture was kept under continuous stirring at room temperature for 22.5 h. The organic layer was washed 2 times with water (3×20 ml), the aqueous layer was washed with dichloromethane (100 ml) and the combined organic layers were dried over anhydrous sodium sulfate, filtered, and concentrated in vacuo at 41° C. The black oily product was subjected to column chromatography (eluent: EtOAc/n-hexane 1/1). A colorless oil resulted which solidified to a white solid.

Yield: 1.92 g (14.1 mmol); 61% of theory $^{1}$H NMR (400 MHz, CHLOROFORM-d) d ppm 1.15 (d, J=6.26 Hz, 6 H) 1.25 (d, J=6.26 Hz, 7 H) 3.81 (s, 6 H) 5.07 (dt, J=12.51, 6.26 Hz, 2 H) 5.81 (s, 2 H) 6.93 (s, 4 H)

$^{13}$C-NMR (100 MHz, CHLOROFORM-d) d ppm 21.6, 52.4, 70.7, 71.4, 131.7, 135.1, 163.4, 164.5, 164.9

IR (ATR) [cm$^{-1}$] 2993, 2955, 1755, 1747, 1722, 1470, 1441, 1333, 1309, 1282, 1248, 1225, 1165, 1142, 1134, 1101, 1038, 1007, 980, 955, 945, 926, 914, 897, 820, 775, 671

Example 3

(2-Hydroxy-ethyl)-bis-[2-((E)-3-methoxycarbonyl-acryloyloxy)-ethyl]-amine

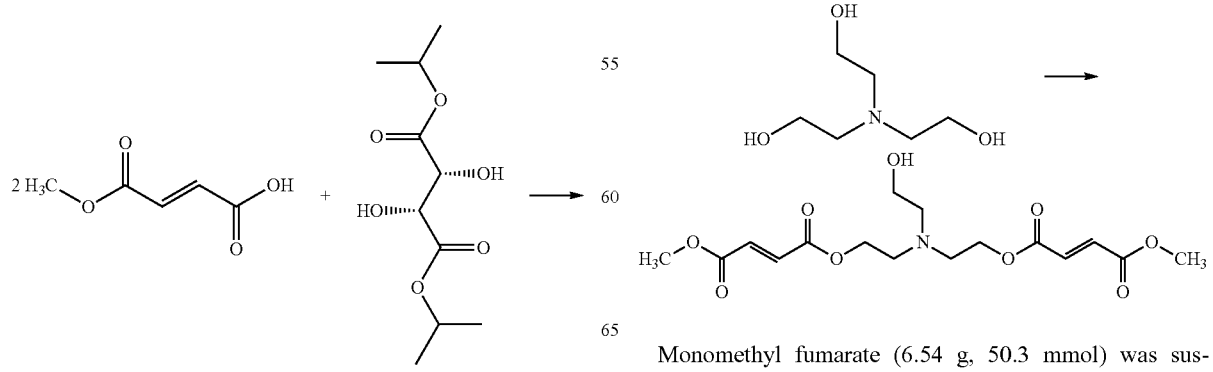

Monomethyl fumarate (6.54 g, 50.3 mmol) was suspended in dichloromethane (100 mL). 4-(dimethylamino)

pyridine (DMAP) (0.41 g, 3.4 mmol) was added and N-ethyl-N'-(3-methylaminopropyl)carbodiimide hydrochloride (EDC) (9.64 g, 50.3 mmol) was added successively to obtain solution 1. In a separate flask triethanolamine (5.00 g, 33.5 mmol) was dissolved in dichloromethane (100 mL) and solution 1 was added drop wise. After completion, the mixture was stirred at RT for 30 min. During this period, the color changed from red-brown to brown. The mixture was diluted with water (150 mL), the two layers were separated and the aqueous phase was extracted twice with dichloromethane (2×250 mL). The organic layer and the extracts were combined, dried over sodium sulfate and concentrated under reduced pressure to yield 6.62 g of a brown oil. The crude product was purified via silicagel chromatography (80 g, 30 μm silica; EtOAc) to yield a light-brown oil which crystallizes to a light-brown solid.

LCMS: chemical purity 96.2% (at 218 nm), $M^+=374$ $^1$H NMR (400 MHz, DMSO-$d_6$) δ: ppm 2.60 (t, J=6.45 Hz, 2 H) 2.81 (t, J=5.67 Hz, 4 H) 3.40 (d, J=4.30 Hz, 2 H) 3.72 (s, 6 H) 4.17 (t, J=5.67 Hz, 4 H) 4.30 (br. s., 1 H) 6.71-6.76 (m, 4 H)

Example 4

Investigation and Comparision of the Kinetics of MMF-Release of the Different Compounds of the Present Invention and DMF During Incubation in Intestinal Fluid of the Minipig 1. Materials
1.1. Test Compounds
Compounds of the present invention were synthesized as described above.
1.2. Intestinal Fluid
Intestinal fluid samples were prepared at CiToxLAB Scantox A/S. The samples were taken from 1 female Göttingen SPF minipig from CiToxLAB Scantox A/S standard stock, originally obtained from Ellegaard Göttingen Minipigs A/S, DK-4261 Dalmose, Denmark. The minipig was 10 months old and the body weight was 21 kg. The minipig was identified by an individual number tagged to the pinna of one ear (animal number is documented in the raw data).

The minipig was fasted for approximately 28 hours before sampling of intestinal fluid. On the day of sampling, the minipig was weighed and anaesthetised by an intramuscular injection in the neck or in the left hind leg (about 0.3 ml per kg body weight) of a mixture of Zoletil 50 Vet., Virbac, France (125 mg tiletamine and 125 mg zolazepam), Rompun Vet., Bayer, Germany (20 mg xylazine/ml, 6.5 ml), Ketaminol Vet., Veterinaria AG, Switzerland (100 mg ketamine/ml, 1.5 ml) and Methadon DAK, Nycomed Danmark, Denmark (10 mg methadon/ml, 2.5 ml).

Intestinal fluid was obtained by flushing one jejunal segment, measuring 30.2 cm, with saline. Intestinal fluid together with saline used for flushing was placed in centrifuge tubes. All samples were frozen at −70° C. and shipped on dry ice to the Sponsor for further use.

2. Analytical Methods
2.1. Quantification of MMF by LC-MS
2.1.1. Analytical Instrument
Instrument: Acquity UPLC system coupled with a TQ detector (triple quadruple mass spectrometer)
UPLC method:
Column: Phenomenex Kinetex C18, 100A, 2.6 μm (150× 4.6 mm)
flow: 0.4 ml/min
split: appr. 100 μl/min to MS
Temperature: 30° C.
solvet system (isocratic):
Solvent A 25% water with 0.1% acetic acid
Solvent B 75% methanol with 0.1% acetic acid
stoptime: 6 min
autosampler temperature: 8° C.
injection volume: 4 μl
retention time: MMF: 4.3 min
MEF: 4.7 min
Mass spectrometry
software: Masslynx 4.1
detection mode: electrospray/negative ions (ESP −)
capillary voltage: 2.3 kV
source temperature: 100° C.
desolvation temperature: 450° C.
cone voltage: 18 V
desolvation gas: $N_2$, 650 L/h
cone gas: $N_2$, 20 L/h
collision gas: argon, appr. $3.3*10^{-3}$ mbar
collision energy: 11 eV
MRM [m/z]: 128.94>85.03 Monomethylfumarate dwell: 200 msec
142.99>99.06 Monoethylfumarate (ISTD) dwell:200 msec
2.1.2. Stock and Calibration Solutions
Stock (SS), working (WS) and calibration solutions of the analyte monomethyl fumarate (MMF) and the internal standard (ISTD) monomethyl fumarate (MEF) were prepared as described below.

$SS_{MMF}$: In a 10 ml volumetric flask, 6.5 mg MMF (Batch: MKRJ0642V/Aldrich) were dissolved in methanol and made up to volume (c=650 μg/ml)

$SS_{ISTD}$: In a 100 ml volumetric flask, 10 mg MEF (Batch: STBC5219V/Aldrich) were dissolved in methanol and made up to volume (c=100 μg/ml)

$WS_{ISTD}$: 100 μl SSISTD were transferred into a 10 ml volumetric flask and made up to volume with acetonitrile (c=1,000 μg/ml);

Calibration solutions were prepared by serial dilution of $SS_{MMF}$; diluted small intestinal fluid (diluted by 1/20 v/v with 50 mM $KH_2PO_4$, pH 6.8; dil IF) was used as matrix. The dilution scheme is given below:

| calibration solution | Preparation | | Concentration [ng/ml] | [μM] |
|---|---|---|---|---|
| cal6500 | 8 μl SSMMF | +792 μl dil IF | 6500 | 50 |
| cal3250 | 50 μl cal6500 | +50 μl dil IF | 3250 | 25 |
| cal650 | 20 μl cal6500 | +180 μl dil IF | 650 | 5.0 |
| cal325 | 50 μl cal650 | +50 μl dil IF | 325 | 2.5 |
| cal65 | 10 μl cal650 | +90 μl dil IF | 65 | 0.5 |

2.1.3. Sample Preparation
50 μl sample (calibration solution or sample of an incubation experiment with MMF prodrugs) was mixed with 50 μl $WS_{ISTD}$, 20 μl formic acid and 100 μl acetonitrile. This mixture was vortexed for 15 sec and centrifuged (13,000 rpm, 3 min). Thereafter, 4 μl of the supernatant were subjected to LC-MS analysis.

2.2. Incubation Experiments with DMF (Reference) and Compounds of the Invention
2.2.1. Stock Solutions
Stock solutions were prepared in DMSO. Concentrations in stock solutions were 5.00, 2.50 and 1.67 mmol for compounds with one, two and three molar MMF equivalents.

| | Sample | | | Concentration | |
|---|---|---|---|---|---|
| Compound | MW | weight [mg] | dissolved in | [mg/ml] | [mmol] |
| DMF | 144.13 | 7.21 | 10 ml DMSO | 0.721 | 5.00 |
| Example 1 | 430.37 | 5.38 | 5 ml DMSO | 1.076 | 2.50 |
| Example 2 | 458.42 | 5.73 | 5 ml DMSO | 1.146 | 2.50 |
| Example 3 | 373.36 | 4.67 | 5 ml DMSO | 0.934 | 2.50 |

2.2.2. Incubation Experiment

In a HPLC glass vial, 8 µl of stock solution were mixed with 792 µl dil IF and the mixture was stirred (250 rpm) in a water bath (T=37° C.).

Immediately after mixing as well as at t=15 min, 30 min, 60 min, 90 min and 120 min, 50 µl were withdrawn and prepared for LC-MS analysis as described in chapter. 2.1.3.

Incubations were continued and in case the result of analysis of the 120 min indicated the presence of remaining intact MMF prodrug, additional samples were taken (t=360 or 420 min and at 1,260 or 1,320 min) and analysed.

3. Results

3.1. Calibration of the Analytical Method

Each calibration solution was analysed two-fold. The second analysis was carried out approx. 18 h after storage of the sample in the autosampler, which was cooled to 8° C. The results demonstrate that the ratio of peak area remains essentially unchanged between the first and the second analysis.

The concentration/peak area ratio data pairs were subjected to regression analysis with 1/x weighting and the resulting calibration equation was used to quantify the MMF content in incubation samples.

| calibration standard | nominal concentration [ng/ml] | Analysis | area/area(ISTD) | Mean | RSD |
|---|---|---|---|---|---|
| cal6500 | 6,500 | 1st analysis | 3.569 | 3.567 | 0.07 |
| | | 2nd analysis | 3.564 | | |
| cal3250 | 3,250 | 1st analysis | 1.710 | 1.681 | 1.73 |
| | | 2nd analysis | 1.652 | | |
| cal650 | 650 | 1st analysis | 0.348 | 0.347 | 0.29 |
| | | 2nd analysis | 0.346 | | |
| cal325 | 325 | 1st analysis | 0.174 | 0.169 | 2.96 |
| | | 2nd analysis | 0.164 | | |
| cal65 | 65 | 1st analysis | 0.036 | 0.035 | 2.86 |
| | | 2nd analysis | 0.034 | | |
| cal0 | 0 | 1st analysis | 0.000 | 0.000 | 0.00 |
| | | 2nd analysis | 0.000 | | |

As can be seen from FIG. 1 the inventive compounds according to Examples 1 and 2 show a modified hydrolyzation compared to DMF. In particular, the release kinetics of the inventive compounds according to Formula (I) are significantly slower than the one of DMF.

Figure 2:
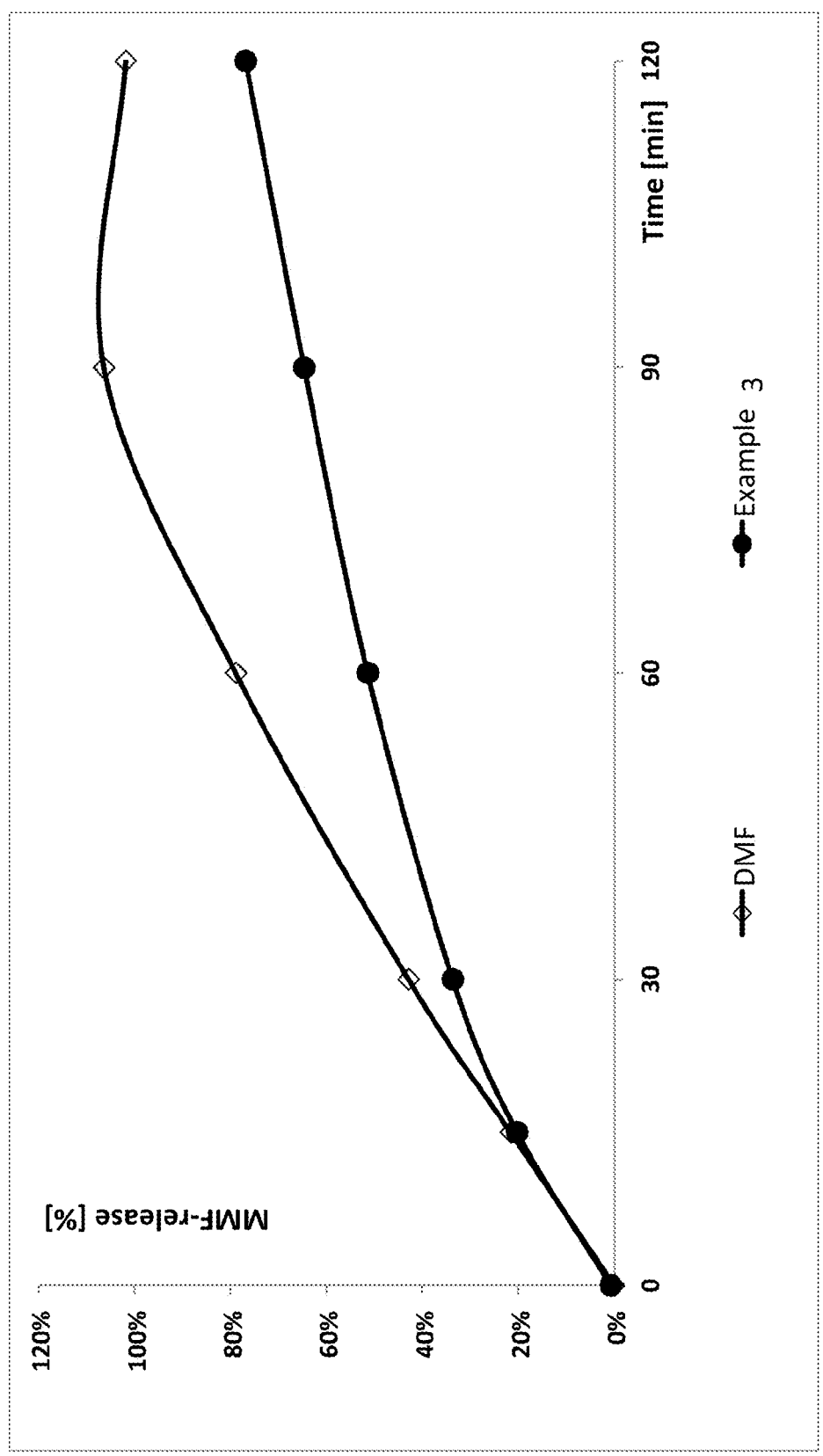
FIG. 2 shows a modified hydrolyzation for the compound of Example 3 as compared to DMF.

Further, as can be seen from FIG. 2 the inventive compound according to Example 3 shows a modified hydrolyzation compared to DMF as well. In particular, the release kinetics of the inventive compound according to Formula (II) is significantly slower than the one of DMF.

The invention claimed is:

1. Compound according to Formula (I) or Formula (II)

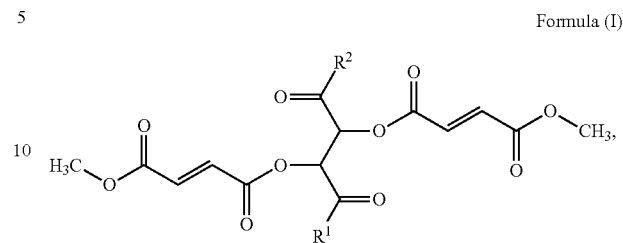

Formula (I)

wherein $R^1$ is $OR^{1'}$ or $NR^{1''}R^{1'''}$ wherein $R^{1'}$ is hydrogen, alkyl with 1 to 6 carbon atoms or cyclic alkyl with 3 to 6 carbon atoms, or wherein $R^{1''}$ and $R^{1'''}$ independently are hydrogen, alkyl with 1 to 6 carbon atoms or cyclic alkyl with 3 to 6 carbon atoms, and $R^2$ is $OR^{2'}$ or $NR^{2''}R^{2'''}$ wherein $R^{2'}$ is hydrogen, alkyl with 1 to 6 carbon atoms or cyclic alkyl with 3 to 6 carbon atoms, or wherein $R^{2''}$ and $R^{2'''}$ independently are hydrogen, alkyl with 1 to 6 carbon atoms or cyclic alkyl with 3 to 6 carbon atoms or wherein $R^1$ and $R^2$ together are $NR^{12}$ forming a cyclic imide, wherein $R^{12}$ is hydrogen, alkyl with 1 to 6 carbon atoms or cyclic alkyl with 3 to 6 carbon atoms;

or

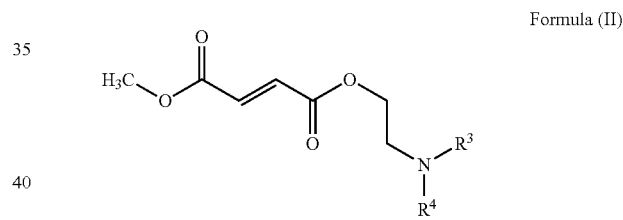

Formula (II)

wherein $R^3$ and $R^4$ are each independently —$(CH_2)_{n'}$—$OR^5$ or —$(CH_2)_{n''}$—CO—$R^6$, wherein n' and n" are each independently 1, 2 or 3, $R^5$ is hydrogen or trans —CO—CH=CH—COOCH$_3$, $R^6$ is $OR^7$ wherein $R^7$ is hydrogen or alkyl with 1 to 4 carbon atoms, or $NR^8R^9$, wherein $R^8$ and $R^9$ are each independently hydrogen or alkyl with 1 to 4 carbon atoms.

2. Compound according to claim 1, wherein $R^1$ and $R^2$ in Formula (I) are $OR^{1'}$ and $OR^{2'}$ wherein $R^{1'}$ and $R^{2'}$ can be independently hydrogen, alkyl with 1 to 6 carbon atoms or cyclic alkyl with 3 to 6 carbon atoms.

3. Compound according to claim 1, wherein in Formula (I) $R^1$ and $R^2$ are $OR^{1'}$ and $OR^{2'}$ and wherein $OR^{1'}$ and $OR^{2'}$ are identical.

4. Compound according to claim 1, wherein $R^1$ and $R^2$ in Formula (I) are $OR^{1'}$ and $OR^{2'}$ and wherein $R^{1'}$ and $R^{2'}$ are hydrogen, ethyl or isopropyl.

5. Compound according to claim 1, wherein the compound according to Formula (I) is selected from the compounds according to any one of Formulae (Ia) to (Ic)

Formula (Ia)

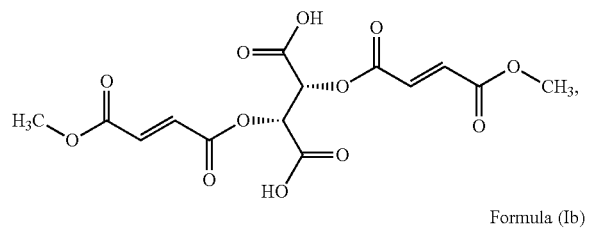

Formula (Ib)

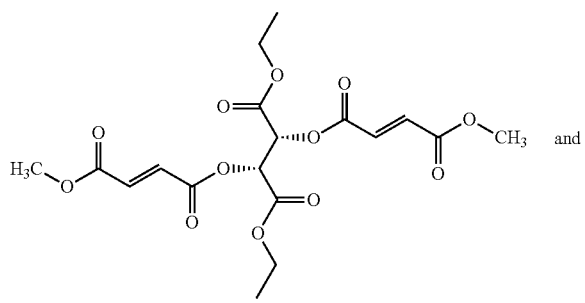 and

Formula (Ic)

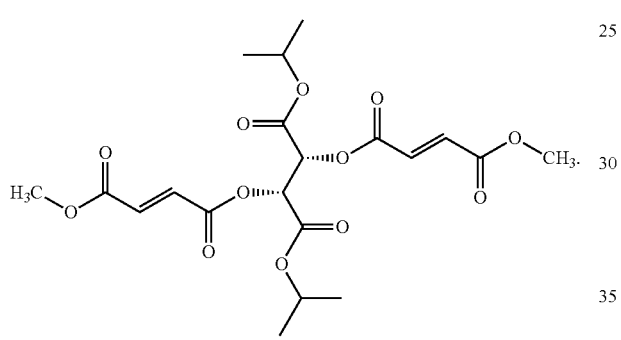

6. Compound according to claim 1, wherein $R^1$ and $R^2$ in Formula (I) are $NR^{1''}R^{1'''}$ and $NR^{2''}R^{2'''}$, wherein $R^{1''}$, $R^{1'''}$, $R^{2''}$ and $R^{2'''}$ independently are hydrogen, alkyl with 1 to 6 carbon atoms or cyclic alkyl with 3 to 6 carbon atoms.

7. Compound according to claim 6, wherein one of $R^{1''}$ and $R^{1'''}$ and one of $R^{2''}$ and $R^{2'''}$ are hydrogen.

8. Compound according to claim 1, wherein $R^1$ and $R^2$ in Formula (I) together are $NR^{12}$ forming a cyclic imide, wherein $R^{12}$ is hydrogen or alkyl with 1 to 3 carbon atoms.

9. Compound according to claim 1, wherein $R^1$ and $R^2$ in Formula (II) are not both trans $-(CH_2)_2-O-CO-CH=CH-COOCH_3$.

10. Compound according to claim 1, wherein one of $R^3$ and $R^4$ in Formula (II) is trans $-(CH_2)_2-O-CO-CH=CH-COOCH_3$.

11. Compound according to claim 1 represented by Formula (IIa)

Formula (IIa)

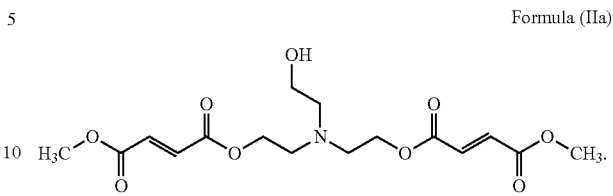

12. Compound according to claim 1, wherein $R^3$ and $R^4$ in Formula (II) are each independently $-(CH_2)_{n'}-OR^5$ or $-(CH_2)_{n''}-CO-R^6$, wherein
    n' and n'' are each independently 1, 2 or 3,
    $R^5$ is hydrogen,
    $R^6$ is $OR^7$ wherein $R^7$ is hydrogen or alkyl with 1 to 4 carbon atoms, or $NR^8R^9$, wherein $R^8$ and $R^9$ are each independently hydrogen or alkyl with 1 to 4 carbon atoms.

13. Compound according to claim 1, wherein in $R^3$ and $R^4$ are each independently $-(CH_2)_{n'}-OR^5$, wherein
    n' is independently 1, 2 or 3, and
    $R^5$ is hydrogen.

14. Compound according to claim 1, wherein in $R^3$ and $R^4$ both are $-(CH_2)_2-OH$ represented by Formula (IIb)

Formula (IIb)

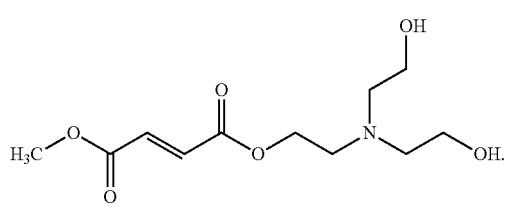

15. Pharmaceutical composition comprising a compound according to claim 1.

16. Pharmaceutical composition according to claim 15, comprising
    (i) 0.01 to 10 mmol of a compound according to any one of the claims 1 to 14 and
    (ii) optionally pharmaceutical excipients.

17. Pharmaceutical composition according to claim 15, wherein the composition is a solid oral dosage form.

18. Pharmaceutical composition according to claim 15, wherein the in-vitro drug release after 2 hours is less than 10%, measured according to USP, Apparatus II, paddle, 0.1 N HCl, 37° C., 50 rpm.

* * * * *